United States Patent [19]

Mokotoff et al.

[11] Patent Number: 4,868,167
[45] Date of Patent: Sep. 19, 1989

[54] NOVEL PEPTIDYL AMINO STEROIDS

[75] Inventors: Michael Mokotoff, Pittsburgh, Pa.; Qing-jiang Liao, Nanjing, China; Lan Wong; Ming Zhao, both of Pittsburgh, Pa.

[73] Assignee: University of Pittsburgh, Pittsburgh, Pa.

[21] Appl. No.: 196,415

[22] Filed: May 20, 1988

[51] Int. Cl.$^4$ .................. A61K 31/58; C07J 41/00
[52] U.S. Cl. ...................................... 514/176; 540/106
[58] Field of Search ........................ 540/106; 514/176

[56] References Cited

U.S. PATENT DOCUMENTS 3,206,456  9/1965  Alburn et al. .................. 540/106

Primary Examiner—Leonard Schenkman
Assistant Examiner—Joseph A. Lipovsky
Attorney, Agent, or Firm—Reed Smith Shaw & McClay

[57] ABSTRACT

The invention relates to novel peptidyl derivatives of Amefalone, Pro-Amefalone, Pro-Pro-Amefalone and D-Ala-Pro-Amefalone, their halide, preferably hydrochloride, salts, to a process for their synthesis and to their use as antiarrhythmic agents.

13 Claims, 1 Drawing Sheet

NOVEL PEPTIDYL AMINO STEROIDS

FIELD OF THE INVENTION

The present invention relates to novel peptidyl amino steroids and more specifically relates to novel peptidyl derivatives of amefalone useful as antiarrhythmic

SUMMARY OF THE INVENTION

The subject invention relates to peptidyl derivatives of amefalone of the structural formula

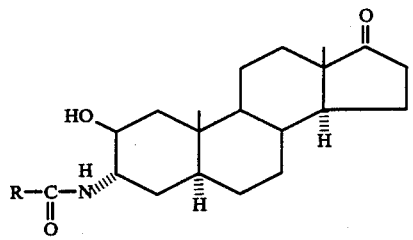

where R is selected from the group consisting of

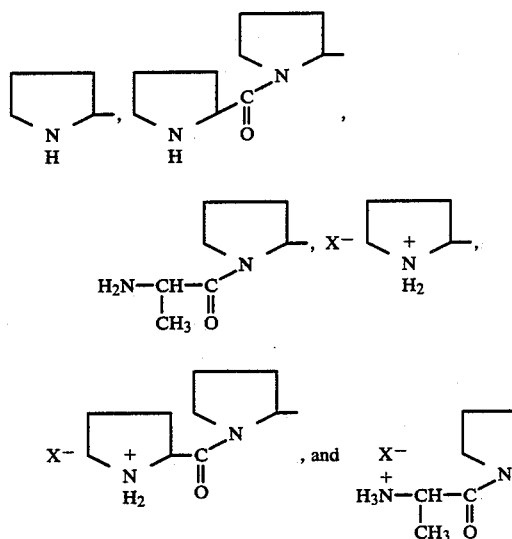

wherein X is a halogen, preferably Cl.

The invention further relates to a process for treating arrhythmia in a mammal comprising administering to the mammal an effective dosage of the peptidyl derivatives of amefalone of the invention to reduce the frequency of arrhythmias being experienced by the mammal.

BACKGROUND OF THE INVENTION

Figure 1:
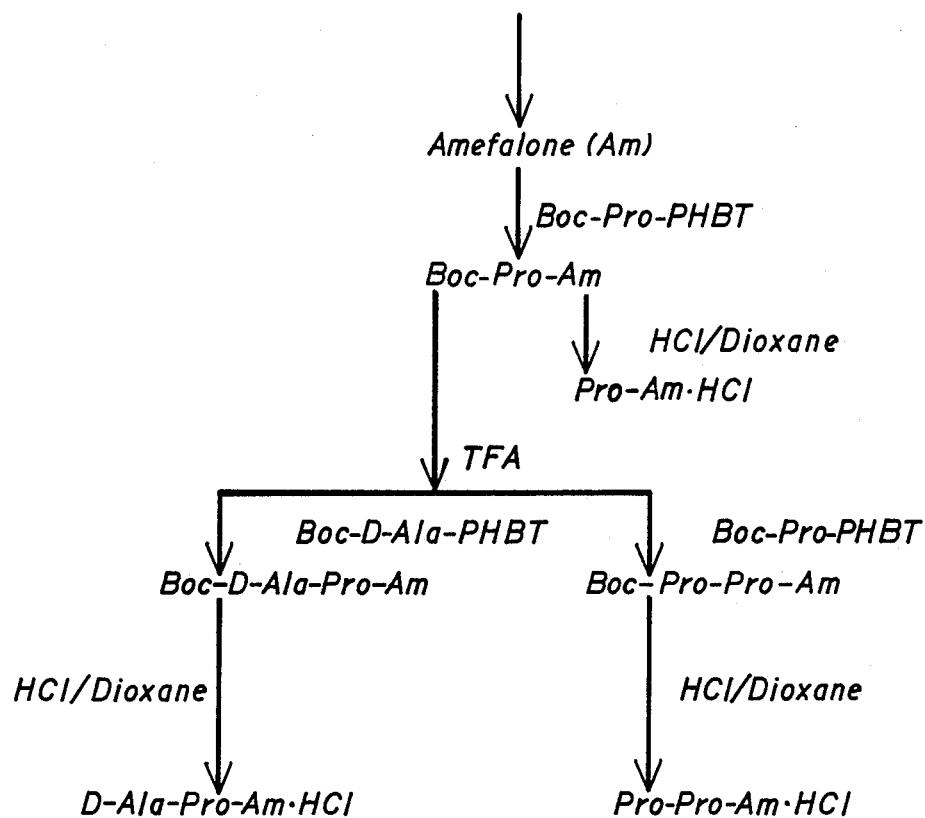
FIG. 1 is a flow scheme for synthesis of preferred peptidyl amefalone compounds of the present invention.

Ventricular fibrillation continues to be a major complication of acute myocardial infarction and is generally considered to be responsible for most of the sudden deaths occurring in the early 1-2 hour pre-hospital phase. In spite of the present antidysrhythmic drugs available, there is still no entirely effective and safe long-term antidysrhythmic agent available. Lignocaine is still considered to be the antidysrhythmic drug of choice during the occurrence of acute life-threatening ventricular dysrhythmias. However, its short duration of action and the necessity of intravenous administration limit its use and indeed its prophylactic value in the early stages of infarction.

Amefalone, 2-β-hydroxy-3 α-amino-5 α-androstan 17-one, is an aminosteroid that has been disclosed to be an active antiarrhythmic agent in mammals by intravenous administration, although it exhibits lesser antiarrhythmic activity if administered orally. Marshall, R. J. and Winslow, E., *Gen. Pharmac.*, 13:315 (1981).

Peptidyl derivatives of amefalone have now been developed which are useful as antiarrhythmic agents, which can be administered either intravenously or orally, and which possess lower toxicity than amefalone.

DETAILED DESCRIPTION OF THE INVENTION

In accordance with the invention, the 3-amino function of amefalone was modified to produce the peptidyl derivatives of amefalone by coupling it to amino acids and peptides in order to protect the primary amine of the amefalone. It is believed that protection of the primary amine of the amefalone alters the normal metabolic pathway that is thought to lead to inactivation of the amefalone. More specifically, the 3-amino function was modified to

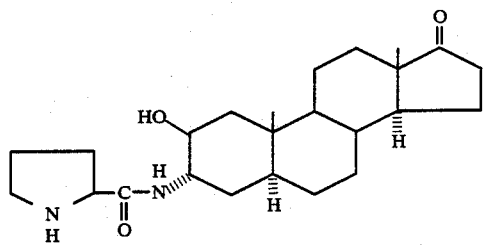

Pro-Amefalone, and its halide salts, preferably

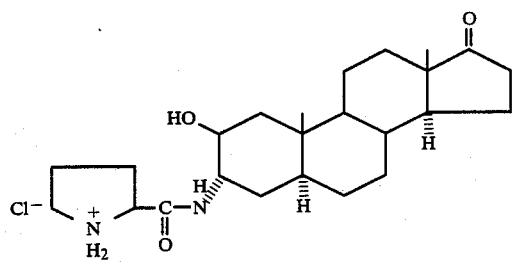

Pro-Amefalone Hydrochloride,

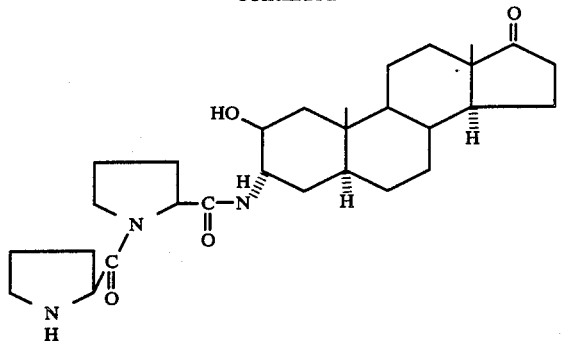

Pro-Pro-Amefalone, and its halide salts, preferably,

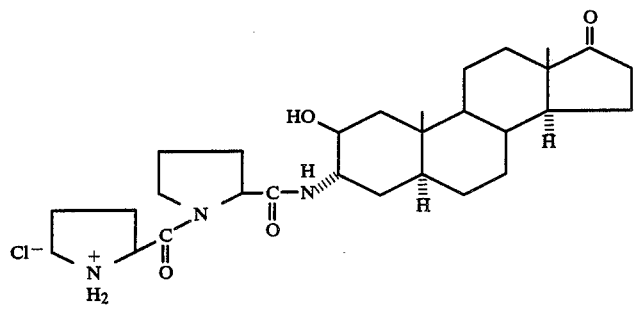

Pro-Pro-Amefalone Hydrochloride, and

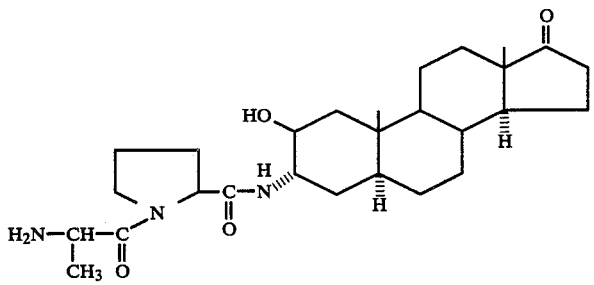

D-Ala-Pro-Amefalone, and its halide salts, preferably,

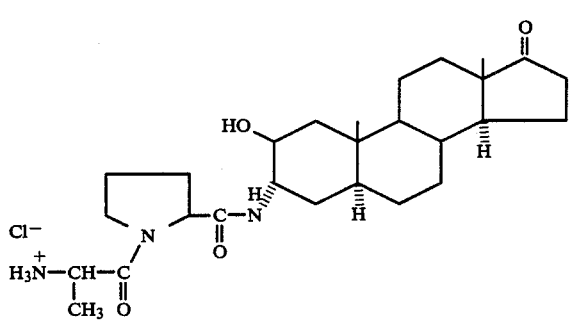

D-Ala-Pro-Amefalone Hydrochloride.

The peptidyl derivatives of amefalone of the present invention may be prepared using known syntheses, and are preferably prepared employing the peptidyl synthesis using polymeric hydroxybenzotriazole (PHBT) described by Mokotoff, M. and Patchornik, A., *Int. J. Peptide Protein Res.*, 21:145 (1983) and by Sheh, L., Mokotoff, M. and Abraham, D. J., *Int. J. Peptide Protein Res.*, 29:509 (1987), the disclosures of which are incorporated herein by reference. Using that synthesis, t-butyloxycarbonyl-proline (Boc-Pro) is first esterified to PHBT using diisopropylcarbodiimide (DIC), and the resulting Boc-Pro-PHBT is then reacted with amefalone to produce Boc-Pro-Amefalone in yields generally from 90% to 99%. The Boc-Pro-Amefalone is then preferably reacted with HCl/dioxane to produce Pro-Amefalone Hydrochloride.

The corresponding dipeptide derivatives, Pro-Pro-Amefalone and D-Ala-Pro-Amefalone, were prepared by reacting the Boc-Pro-Amefalone with trifluoroacetic acid (TFA) to remove the Boc group followed by reaction with either Boc-D-Ala-PHBT or Boc-Pro-PHBT to produce Boc-D-Ala-Pro-Amefalone or Boc-Pro-Pro-Amefalone, respectively. Removal of the Boc group, preferably by HCl/dioxane, yields D-Ala-Pro-Amefalone Hydrochloride and Pro-Pro-Amefalonce Hydrochloride in yields generally of from 80% to 95%.

A preferred flow scheme using this synthesis for the preparation of the preferred peptidyl amino steroids Pro-Amefalone Hydrochloride, Pro-Pro-Amefalone Hydrochloride and D-Ala-Pro-Amefalone Hydrochloride is set forth in FIG. 1.

EXPERIMENTAL STUDIES

EXAMPLE 1: Synthesis of L-Pro-Amelfalone.HCl 10 grams of Boo-L-Pro-PHBT was placed in a 200 ml flask with 60 ml of dimethylformamide (DMF) and was shaken at room temperature for 15 minutes to allow the polymer to swell. 2.7 g. of Amefalone HCl was suspended in 15 ml. of DMF and diisopropylethylamine (DIEA, 1.16 g.), and the suspension was added to the flask and shaken at room temperature for 8 hours. Thin layer chromatography showed that there was also a small amount of Amefalone in the solution. After filtration of the polymer, the polymer was washed 4 times, each time using 40 ml. of $CH_2Cl_2$. The combined washing solution was evaporated to near dryness to obtain an oil. The residue was crystallized with $CHCl_3$ and ether to give 3.95 g. Recrystallization from $CHCl_3$ and ether gave 2.90 g. Boc-L-Pro-Amefalone.

The Boc-L-Pro-Amefalone was placed in a 25 ml bottle with 10 ml of 3N HCl in dioxane and was stirred at room temperature for 30 minutes. The solution was dried by evaporating the solvent. The residue was triturated and washed twice with 10 ml of acetone. The solid obtained was crystallized from methanol-acetone to give L-Pro-Amefalone HCl, 0.43 g., with a yellow color. Recrystallization of the yellow product again yielded 0.34 g. of L-Pro-Amefalone HCl.

EXAMPLE 2: Synthesis of L-Pro-L-Pro-Amelfalone.HCl 0.82 grams of Boc-L-Pro-Amefalone was stirred with 10 ml of TFA at room temperature for 30 minutes. Evaporation of the excess TFA and trituration of the residue with ether gave a solid which was dried under vacuum overnight over $P_2O_5$ and NaOH pellets.

The Boc-L-Pro-PHBT was next shaken with 10 ml of $CH_2Cl_2$ for 30 minutes to allow the polymer to swell, and the solution of the TFA salt of L-Pro-Amefalone was dissolved in 10 ml of $CH_2Cl_2$ and 0.4 g. of DIEA. The $CH_2Cl_2$ solution was added to the polymer. The mixture was shaken at room temperature for 6 hours and filtered. The polymer was washed with $CH_2Cl_2$. The combined $CH_2Cl_2$ solution was evaporated to dryness. The residue was redissolved in 70 ml of $CH_2Cl_2$ and was washed successively with cold 95% citric acid, 5% sodium carbonate and distilled water, then dried over sodium sulfate. Evaporation of the $CH_2Cl_2$ gave an oily residue of Boc-L-Pro-L-Pro-Amefalone.

The Boc-L-Pro-L-Pro-Amefalone was stirred with 10 ml of 3.6N HCl in dioxane at room temperature for 30 minutes. Evaporation of the solvent and crystallization of the residue from methanol and ether yielded 0.76 g. of L-Pro-L-Pro-Amefalone HCl.

EXAMPLE 3: Synthesis of D-ala-L-Pro-Amefaloe HCl 1.18 gram of Boc-L-Pro-Amefalone was stirred with 15 ml of TFA at room temperature for 30 minutes. The excess TFA was evaporated. The residue was triturated with ether. The solidified residue was dried overnight under a vacuum over $P_2O_5$ and NaOH pellets.

The Boc-D-Ala-PHBT was then shaken with 20 ml of $CH_2Cl_2$ at room temperature for 15 minutes to allow the polymer to swell. The above TFA salt of L-Pro-Amefalone was dissolved in a solution of 8 ml of $CH_2Cl_2$ and 0.79 of DIEA. The TFA salt solution was added to the polymer and the mixture was shaken at room temperature for 6 hours. After filtration, the polymer was washed with $CH_2Cl_2$. The $CH_2Cl_2$ solution was evaporated to near dryness and the residue was redissolved into $CHCl_{13}$, and the solution was washed successively with cold 10% citric acid, 5% $Na_2CO_3$ and water, then dried over $Na_2SO_4$. The $CHCl_3$ solution was evaporated to near dryness, affording Boc-D-Ala-L-Pro-Amefalone as an oil. 1.52 grams of this oil was stirred with 15 ml of 3.6N HCl in dioxane at room temperature for 30 minutes. Evaporation of the solvent and crystallization of the residue from ethanol, dioxane and acetone yielded 1.04 g. of D-Ala-L-Pro-Amefalone HCl.

BIOLOGICAL TESTING

Samples of the L-Pro-Amefalone.HCl and L-Pro-L-Pro-Amefalone.HCl were tested as antiarrhythmic agents, with male Wistar rats subjected to ischemia induced arrhythmias following the general protocol described by Marshall, R. J., Muir, A. W., and Winslow, E., *Br. J. Pharmac.*, 74:381 (1981), the disclosure of which is incorporated herein by reference. The results of the testing are presented in Tables 1 and 2 below. As the results indicate, these peptidyl derivatives of amefalone when administered intravenously compared favorably with Amefalone itself, both with regard to antiarrhythmic and hemodynamic effects.

TABLE 1

| | | Ischemia Induced Arrhythmias In Anesthetized Rats | | | | | | | |
|---|---|---|---|---|---|---|---|---|---|
| | Number of | Total | Non-VT | VT | VT | | % Incidence | | |
| | Rats Tested | PVS | PVS | PVS | No Episodes | Duration(s) | VT | VF | Death |
| Controls | 18 | 361 ± 108 (14) | 103 ± 24 (14) | 258 ± 106 (14) | 7.43 ± 2.56 (14) | 29.0 ± 11.0 (11) | 83 | 22 | 22 |
| Amefalone | 9 | 271 ± 130 (9) | 129 ± 37 (9) | 142 ± 138 (9) | 1.33 ± 0.83* (9) | 37.5 ± 36.1 (3) | 33* | 0 | 0 |
| Pro-Amefalone | 10 | 236 ± 180 (10) | 217 ± 173 (10) | 19 ± 8* (10) | 2.20 ± 1.26$^a$ (10) | 3.07 ± 1.21* (5) | 50 | 0 | 0 |
| Pro-Pro-Amefalone | 10 | 206 ± 152 (9) | 109 ± 65 (9) | 97 ± 97 (9) | 0.78 ± 0.78* (9) | 82.64+ (1) | 20** | 10 | 10 |

+6.47 s of VT + 19.15 s VF
$^a$, p = 0.07
*, p < 0.05
**, p < 0.01
PVS = premature ventricular systales
VT = ventricular tachycardia
VF = ventricular fibrillation

TABLE 2

Effects On Blood Pressure (BP) (min + 2) and Heart Rate (HR) (beats/min.)
In Anesthetized Rats

| | Pre-Treatment | | Immediate Effects | | 15 min. Post-Treatment | |
|---|---|---|---|---|---|---|
| | HR | BP | HR | BP | HR | PB |
| Controls | 424 ± 14 | 95 ± 4/70 ± 4 | — | — | 423 ± 11 | 97 ± 4/70 ± 4 |
| Amefalone | 422 ± 8 | 111 ± 10/86 ± 11 | 390 ± 14 | 90 ± 7/61 ± 7 | 396 ± 17 | 128 ± 9/98 ± 9 |
| Pro-Amefalone | 415 ± 11 | 85 ± 7/60 ± 8 | 396 ± 11 | 82 ± 8/56 ± 8 | 406 ± 14 | 89 ± 6/61 ± 7 |

TABLE 2-continued

| | Effects On Blood Pressure (BP) (min + 2) and Heart Rate (HR) (beats/min.) In Anesthetized Rats | | | | | |
|---|---|---|---|---|---|---|
| | Pre-Treatment | | Immediate Effects | | 15 min. Post-Treatment | |
| | HR | BP | HR | BP | HR | PB |
| Pro-Pro-Amefalone | 420 ± 18 | 101 ± 7/74 ± 7 | 408 ± 16 | 97 ± 6/70 ± 7 | 440 ± 19 | 104 ± 7/731 ± 8 |

Although the invention has been described in detail for the purposes of illustration, it is to be understood that such detail is solely for that purpose and that variations can be made therein by those skilled in the art without departing from the spirit and scope of the invention except as it may be limited by the claims.

What is claimed is:

1. A compound of the structural formula

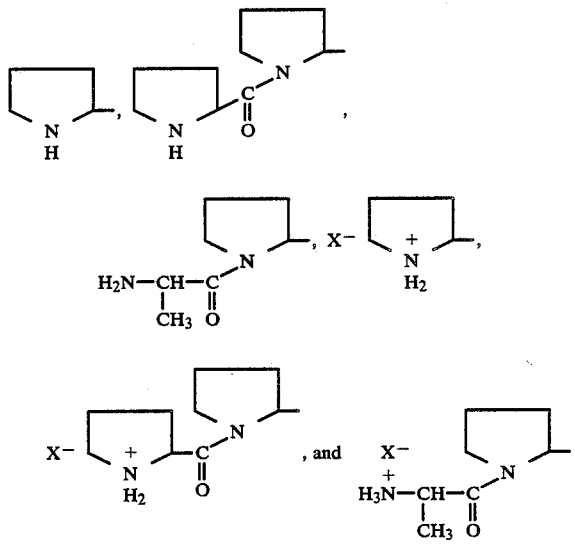

where R is selected from the group consisting of

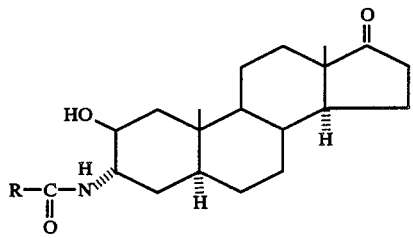

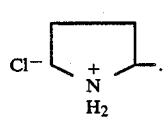

where X is a halogen.

2. The compound of claim 1 wherein X is Cl.
3. The compound of claim 1 wherein R is

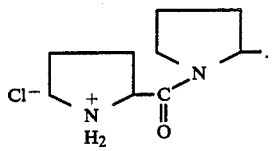

5. The compound of claim 1 wherein R is

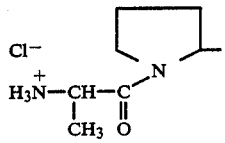

6. The compound of claim 1 wherein R is

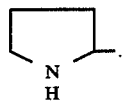

7. The compound of claim 1 wherein R is

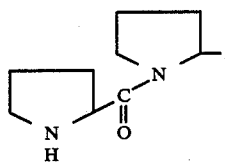

8. The compound of claim 1 wherein R is

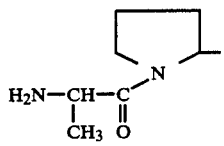

9. A method for treating arrhythmia in a mammal comprising administering to the mammal a dosage of a compound of claim 1 in an amount effective to reduce the frequency of arrhythmias being experienced by the mammal.

10. The method of claim 9 wherein the administration is intravenous.

11. The method of claim 9 wherein the dosage of active agent is between 2 and 10 mg/kg.

12. The method of claim 9 wherein the administration is oral.

13. The method of claim 10 wherein the dosage of active agent is between 20 and 100 mg/kg.

* * * * *

UNITED STATES PATENT AND TRADEMARK OFFICE
CERTIFICATE OF CORRECTION

PATENT NO. : 4,868,167
DATED : September 19, 1989
INVENTOR(S) : Michael Mokotoff, et al.

It is certified that error appears in the above—identified patent and that said Letters Patent is hereby corrected as shown below:

At column 1, line 7, the word -- agents -- should be inserted after the word "antiarrhythmic";

At column 2, line 37, the word -- produce -- should be inserted after the word "to";

At column 4, line 53, the phrase -- Pro-Pro-Amefalonce -- should be "Pro-Pro-Amefalone";

At column 4, line 62, the term -- Boo-L-ProPHBT -- should be "Boc-L-Pro-PHBT";

At columns 5 and 6, Table 1, the explanatory note reading -- +6.47 s of VT + 19.15 s VF -- should be "+63.47 s of VT + 19.5 s VF"; and At column 6, line 3, the term -- D-ala-L-Pro-Amefaloe·HCl -- should be "D-ala-L-Pro-Amefalone·HCl".

Signed and Sealed this

Eleventh Day of September, 1990

Attest:

HARRY F. MANBECK, JR.

Attesting Officer         Commissioner of Patents and Trademarks

UNITED STATES PATENT AND TRADEMARK OFFICE
CERTIFICATE OF CORRECTION

PATENT NO. : 4,868,167

DATED : September 19, 1989

INVENTOR(S) : Michael Mokotoff, et al.

It is certified that error appears in the above-identified patent and that said Letters Patent is hereby corrected as shown below:

At column 5, line 29, the -- , -- should be replaced by a ".";

At column 5, line 29, the phrase -- and the solution of the -- should be replaced by the word "The";

At column 6, line 9, the term -- P205 -- should be "$P_2O_5$";

At column 6, line 14, the term -- .79 -- should be ".79g."; and

At column 6, line 19, the term -- CHCl13 -- should be "$CHCl_3$".

Signed and Sealed this

Third Day of December, 1991

Attest:

HARRY F. MANBECK, JR.

*Attesting Officer*     *Commissioner of Patents and Trademarks*